US011530991B2

(12) United States Patent
Chen et al.

(10) Patent No.: US 11,530,991 B2
(45) Date of Patent: Dec. 20, 2022

(54) APPARATUS AND METHOD OF DETERMINING BIOLOGICAL PROPERTY WITH TEST STRIP ADAPTOR

(71) Applicant: iXensor Co., LTD., Taipei (TW)

(72) Inventors: Yenyu Chen, Taipei (TW); Chien Hsun Chen, Taipei (TW); Yao Ching Tsai, Taipei (TW)

(73) Assignee: IXENSOR CO., LTD.

( * ) Notice: Subject to any disclaimer, the term of this patent is extended or adjusted under 35 U.S.C. 154(b) by 42 days.

(21) Appl. No.: 17/059,458

(22) PCT Filed: May 29, 2019

(86) PCT No.: PCT/CN2019/088984
§ 371 (c)(1),
(2) Date: Nov. 29, 2020

(87) PCT Pub. No.: WO2019/228393
PCT Pub. Date: Dec. 5, 2019

(65) Prior Publication Data
US 2021/0364445 A1 Nov. 25, 2021

Related U.S. Application Data

(60) Provisional application No. 62/677,685, filed on May 30, 2018.

(51) Int. Cl.
*G06F 21/62* (2013.01)
*G06T 7/90* (2017.01)
(Continued)

(52) U.S. Cl.
CPC ......... *G01N 21/78* (2013.01); *G06F 21/6245* (2013.01); *G06K 9/6201* (2013.01);
(Continued)

(58) Field of Classification Search
CPC .......... G01N 21/78; G01N 2021/7759; G01N 33/48; G01N 33/58; G06F 21/6245;
(Continued)

(56) References Cited

U.S. PATENT DOCUMENTS

2012/0244624 A1* 9/2012 Hsiao ................. G01N 21/8483
436/95
2013/0273528 A1 10/2013 Ehrenkranz
(Continued)

FOREIGN PATENT DOCUMENTS

CN 106255878 A 12/2016
CN 206497121 U 9/2017
(Continued)

OTHER PUBLICATIONS

International Search Report and Written Opinion of the International Searching Authority, International application No. PCT/CN2019/088984, dated Aug. 30, 2019.

*Primary Examiner* — Alazar Tilahun
(74) *Attorney, Agent, or Firm* — Su IP Consulting (57) ABSTRACT

A method to process an image to determine a biological property associated with a test strip (221, 313, 323, 333, 413, 423, 513, 523) in a test strip adaptor (120, 220, 620, 720). The method includes receiving the image captured by a mobile computing device (100, 600, 700) and determining whether the received image includes sensitive information. In response to determining that the image includes sensitive information, the method further includes overwriting the image with a later received image before the image can be saved as a file. In response to determining that the image does not include sensitive information, the method further includes identifying a characteristic configuration associated with the test strip (221, 313, 323, 333, 413, 423, 513, 523)
(Continued)

and determining the biological property based on the image and the characteristic configuration.

20 Claims, 8 Drawing Sheets

(51) Int. Cl.
      *G06T 7/00* (2017.01)
      *G06K 9/62* (2022.01)
      *G06K 9/00* (2022.01)
      *G01N 21/78* (2006.01)
      *G16H 40/67* (2018.01)
      *G16H 10/40* (2018.01)
      *G16H 10/60* (2018.01)
      *G16H 30/20* (2018.01)
      *H04N 5/225* (2006.01)
      *G06V 40/16* (2022.01)
      *G01N 21/77* (2006.01)
      *G06F 9/54* (2006.01)

(52) U.S. Cl.
    CPC .............. *G06T 7/0012* (2013.01); *G06T 7/90* (2017.01); *G06V 40/161* (2022.01); *G16H 10/40* (2018.01); *G16H 10/60* (2018.01); *G16H 30/20* (2018.01); *G16H 40/67* (2018.01); *H04N 5/2256* (2013.01); *G01N 2021/7759* (2013.01); *G06F 9/541* (2013.01); *G06T 2207/30201* (2013.01); *G06V 2201/03* (2022.01)

(58) Field of Classification Search
    CPC ..... G06F 9/541; G06K 9/6201; G06T 7/0012; G06T 7/90; G06T 2207/30201; G06V 40/161; G06V 2201/03; G16H 10/40; G16H 10/60; G16H 30/20; G16H 40/67; H04N 5/2256
    See application file for complete search history.

(56) References Cited

U.S. PATENT DOCUMENTS

| | | | |
|---|---|---|---|
| 2014/0072189 A1* | 3/2014 | Jena | A61B 5/6898 382/128 |
| 2014/0170757 A1* | 6/2014 | Tsai | G01N 21/78 436/55 |
| 2014/0296112 A1* | 10/2014 | O'Driscoll | G01J 3/0272 250/206 |
| 2015/0031412 A1* | 1/2015 | Quilter | G01N 21/27 455/575.1 |
| 2015/0177147 A1* | 6/2015 | Mangan | G01N 21/6428 382/133 |

FOREIGN PATENT DOCUMENTS

| | | |
|---|---|---|
| TW | 201441619 A | 11/2014 |
| TW | 201506381 A | 2/2015 |

* cited by examiner

APPARATUS AND METHOD OF DETERMINING BIOLOGICAL PROPERTY WITH TEST STRIP ADAPTOR

CROSS-REFERENCE TO RELATED APPLICATIONS

The present application is a U.S. national stage filing under 35 U.S. C. § 371 of International Application No. PCT/CN2019/088984, filed May 29, 2019, which claims the benefit of U.S. Provisional Application No. 62/677,685 filed on May 30, 2018. The International Application and the U.S. Provisional Application above are incorporated by reference in their entirety.

BACKGROUND

In recent years, in-vitro diagnosis (IVD) devices, especially blood glucose meters, have gained wide adoption among patients with chronic diseases. In order to take measurements, patients usually have to carry standalone IVD devices with them at all times.

For typical IVD measurements, test strips consisting enzyme and reagent are used. Upon receiving the sample fluid, the test strip's characteristics, such as electrical impedance or color, change according to the concentration of the targeted analyte, such as blood glucose or blood cholesterol.

Optochemistry-based IVD systems usually comprises test strips that change color according to the concentration of analyte received, specific light sources that illuminate on strips, optical sensors that detect scattering light, and light-isolating cases.

These existing IVD devices tend to work with a particular type of test strip. For patients needing to conduct multiple tests involving different types of test strips, they would be required to obtain and carry multiple IVD devices with them. In addition, the patients also prefer these IVD devices having privacy protection functions.

SUMMARY

In examples of the present disclosure, a method to process an image to determine a biological property associated with a test strip in a test strip adaptor is disclosed. The method includes receiving the image captured by a mobile computing device and determining whether the image includes sensitive information. In response to determining that the image includes sensitive information, the method includes overwriting the image with a later received image before the image can be saved as a file. In response to determining that the image does not include sensitive information, the method further includes identifying a characteristic configuration associated with the test strip and determining the biological property based on the image and the characteristic configuration.

In other examples of the present disclosure, a non-transitory computer-readable storage medium that includes a set of instructions which, in response to execution by a processor of a computer system, cause the processor to implement a method to process an image to determine a biological property associated with a test strip in a test strip adaptor is disclosed. The method includes receiving the image captured by a mobile computing device and determining whether the image includes sensitive information. In response to determining that the image includes sensitive information, the method includes overwriting the image with a later received image before the image can be saved as a file. In response to determining that the image does not include sensitive information, the method further includes identifying a characteristic configuration associated with the test strip and determining the biological property based on the image and the characteristic configuration.

In yet other examples of the present disclosure, a computer system configured to process an image to determine a biological property associated with a test strip in a test strip adaptor is disclosed. The computer system comprises a processor and a non-transitory computer-readable medium. The non-transitory computer-readable medium stores instructions that, in response to execution by the processor, cause the processor to receive the image captured by a mobile computing device and determine whether the image includes sensitive information. In response to determining that the image includes sensitive information, the non-transitory computer-readable medium stores additional instructions that, in response to execution by the processor, cause the processor to overwrite the image with a later received image before the image can be saved as a file. In response to determining that the image does not include sensitive information, the non-transitory computer-readable medium stores additional instructions that, in response to execution by the processor, cause the processor to identify a characteristic configuration associated with the test strip and determine the biological property based on the image and the characteristic configuration.

In other examples of the present disclosure, a non-transitory computer-readable storage medium that includes a set of instructions which, in response to execution by a processor of a computer system, cause the processor to implement a method to process an image to determine a biological property associated with a test strip in a test strip adaptor is disclosed. The method includes receiving the image captured by a mobile computing device and determining whether the image includes sensitive information. In response to determining that the image includes sensitive information, the method includes overwriting the image with a later received image before the image can be saved as a file. In response to determining that the image does not include sensitive information, the method further includes identifying a characteristic configuration associated with the test strip and determining the biological property based on the image and the characteristic configuration.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are therefore not to be considered limiting of its scope. The disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components and same numerals typically identify same components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated herein.

Figure 1:
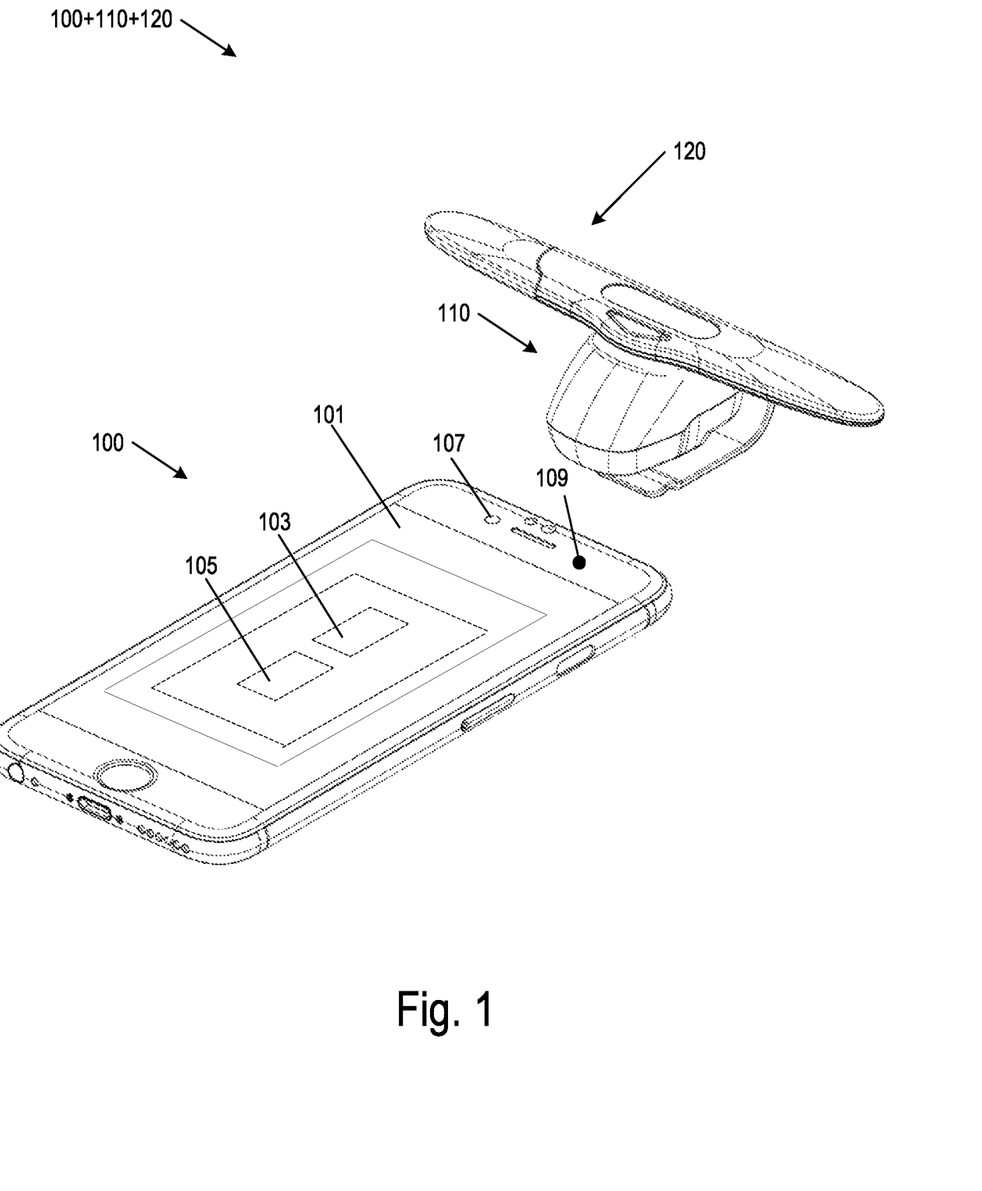
FIG. 1 illustrates an exploded top perspective view of mobile computing device 100, mobile computing device adaptor 110 and test strip adaptor 120, according to some embodiments of the present disclosure.

FIG. 1 illustrates an exploded top perspective view of mobile computing device 100, mobile computing device adaptor 110 and test strip adaptor 120, according to some embodiments of the present disclosure. Mobile computing device 100 includes processor 103 and memory 105. In some embodiments, mobile computing device 100 also includes screen 101, camera 107 and light intensity sensor 109 disposed on a same surface of mobile computing device 100. Mobile computing device adaptor 110 is configured to couple to mobile computing device 100 and test strip adaptor 120 is configured to couple to mobile computing device adaptor 110.

Figure 2:
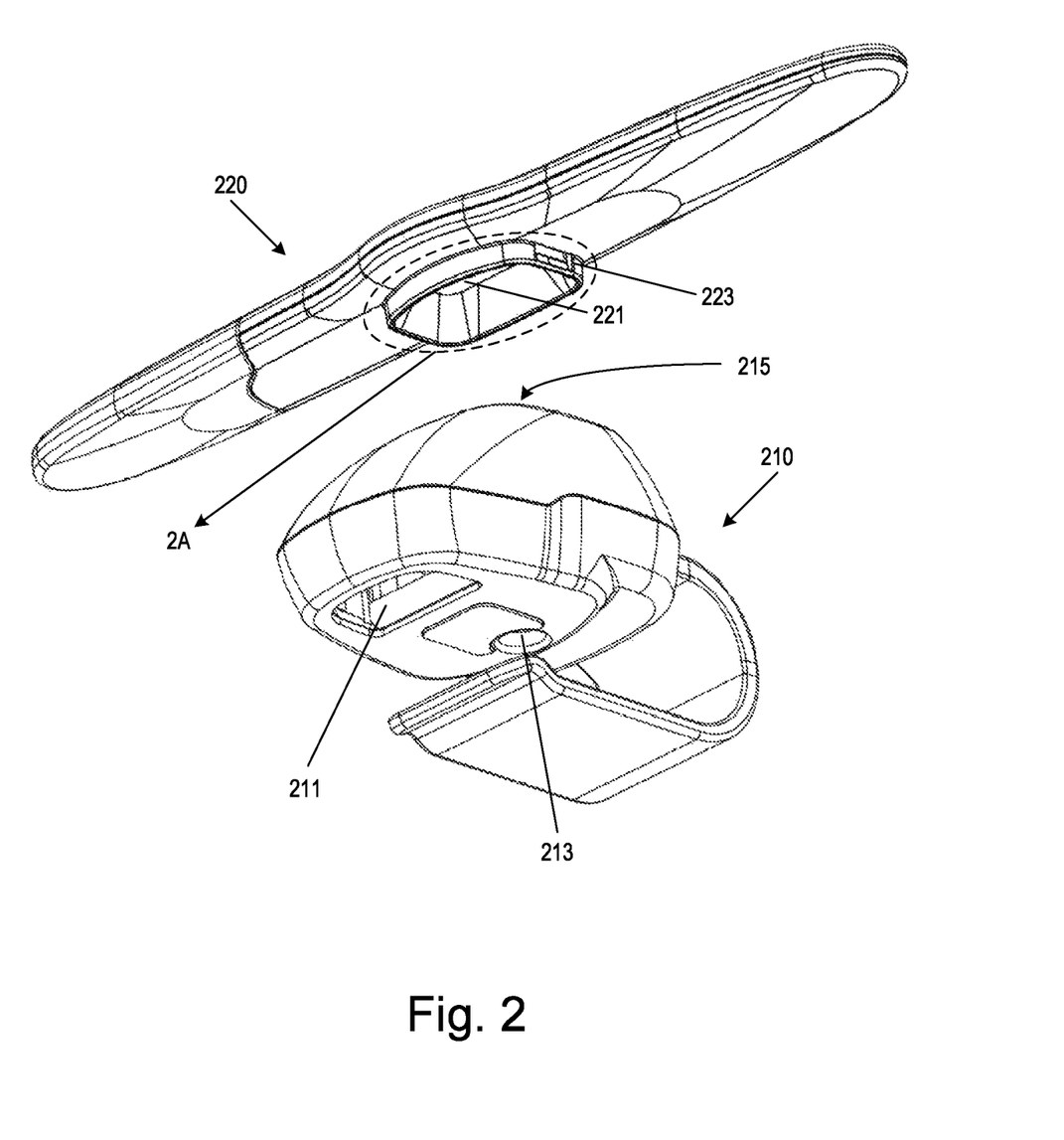
FIG. 2 illustrates an exploded bottom perspective view of mobile device adaptor 210 and test strip adaptor 220, according to some embodiments of the present disclosure.

FIG. 2 illustrates an exploded bottom perspective view of mobile computing device adaptor 210 and test strip adaptor 220, according to some embodiments of the present disclosure. Mobile computing device adaptor 210 may be mobile computing device adaptor 110 and test strip adaptor 220 may be test strip adaptor 120. In some embodiments, mobile computing device adaptor 210 defines light port 211, camera hole 213 and top opening 215. In conjunction with FIG. 1, light port 211 may be disposed over a portion of screen 101 and camera hole 213 may be disposed over camera 107.

In some embodiments, test strip adaptor 220 includes test strip 221 and test strip opening 223 to view test strip 221. In some embodiments, test strip opening 223 is configured to couple to top opening 215.

In some embodiments, in conjunction with FIG. 1, light transmitted from screen 101 is configured to travel through light port 211, top opening 215, and test strip opening 223 to test strip 221. The light transmitted from screen 101 may illuminate a reaction area of test strip 221. In conjunction with FIG. 1, camera 107 is configured to capture an image of the reaction area through test strip opening 223, top opening 215, and camera hole 213.

Figure 3:
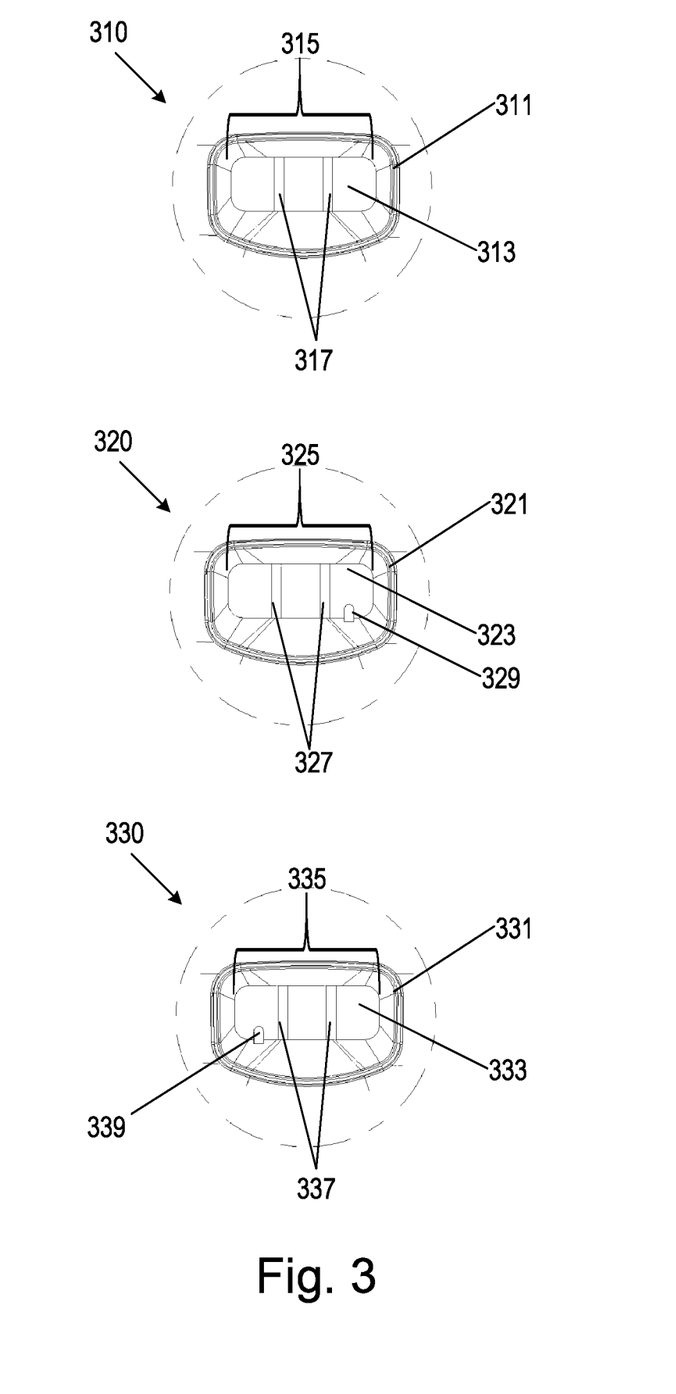
FIG. 3 illustrates a first bottom perspective view 310 of a part of a first type of test strip adaptor, a second bottom perspective view 320 of a part of a second type of test strip adaptor, and a third bottom perspective view 330 of a part of a third type of test strip adaptor, according to some embodiments of the present disclosure.

In conjunction with FIG. 2, FIG. 3 illustrates a first bottom perspective view 310 of 2A of a first type of test strip adaptor 220 in FIG. 2, according to some embodiments of the present disclosure. Similarly, FIG. 3 also illustrates a second bottom perspective view 320 of 2A of a second type of test strip adaptor 220 in FIG. 2, and a third bottom perspective view 330 of 2A of a third type of test strip adaptor 220 in FIG. 2, according to some embodiments of the present disclosure.

In conjunction with FIG. 2, from the user perspective (e.g., a patient), in some embodiments, the user usually purchases test strip adaptor 220 from the pharmacy. Test strip 221 enclosed in test strip 220 is configured to test a specific biological property of the user. Therefore, to detect different biological properties, various types of test strips are needed, so as their corresponding test strip adaptors. For example, the first type of test strip adaptor is configured to detect a first biological property (e.g., glucose concentration). Similarly, the second type of test strip adaptor is configured to detect a second biological property (e.g., ketone concentration), and the third type of test strip adaptor is configured to detect a third biological property (e.g., proteins concentration). However, it becomes challenging to manually select appropriate applications to calculate these concentrations from an user interface. Therefore, it is preferable that the images of the reaction areas obtained from the first type of test strip adaptor, the second type of test strip adaptor, and the third type of test strip adaptor are different to actuate their corresponding appropriate applications to calculate the biological property concentration.

In some embodiments, the first type of test strip adaptor defines test strip opening 311 and encloses test strip 313 to determine the first biological property. In some embodiments, reaction area 315 of test strip 313 is exposed from test strip opening 310. Reaction area 315 may include reaction bar 317 with a reaction agent sensitive to the first biological property. In conjunction with FIG. 1 and FIG. 2, one or more image of reaction area 315 may be captured by camera 107 through test strip opening 311, top opening 215, and camera hole 213. In some embodiments, the captured image may include an image of reaction bar 317. The captured images may be analyzed to determine the first biological property.

In some embodiments, the second type of test strip adaptor defines test strip opening 321 and encloses test strip 323 to determine the second biological property. In some embodiments, reaction area 325 of test strip 323 is exposed from test strip opening 321. Reaction area 325 may include reaction bar 327 with a reaction agent sensitive to the second biological property. In some embodiments, the second type of test strip adaptor further includes protrusion 329 over reaction area 325. In some embodiments, protrusion 329 is disposed adjacent to a first side of reaction bar 327. In conjunction with FIG. 1 and FIG. 2, one or more image of reaction area 325 may be captured by camera 107 through test strip opening 321, top opening 215, and camera hole 213. In some embodiments, the captured image may include an image of reaction bar 327 and an image of protrusion 329. The captured images may be analyzed to determine the second biological property.

In some embodiments, the third type of test strip adaptor defines test strip opening 331 and encloses test strip 333 to determine the third biological property. In some embodiments, reaction area 335 of test strip 333 is exposed from test strip opening 331. Reaction area 335 may include reaction bar 337 with a reaction agent sensitive to the third biological property. In some embodiments, the third type of test strip adaptor further includes protrusion 339 over reaction area 335. In some embodiments, protrusion 339 is disposed adjacent to a second side of reaction bar 337. In conjunction with FIG. 1 and FIG. 2, one or more image of reaction area 335 may be captured by camera 107 through test strip opening 331, top opening 215, and camera hole 213. In some embodiments, the captured image may include an image of reaction bar 337 and an image of protrusion 339. The captured images may be analyzed to determine the third biological property.

Figure 4:
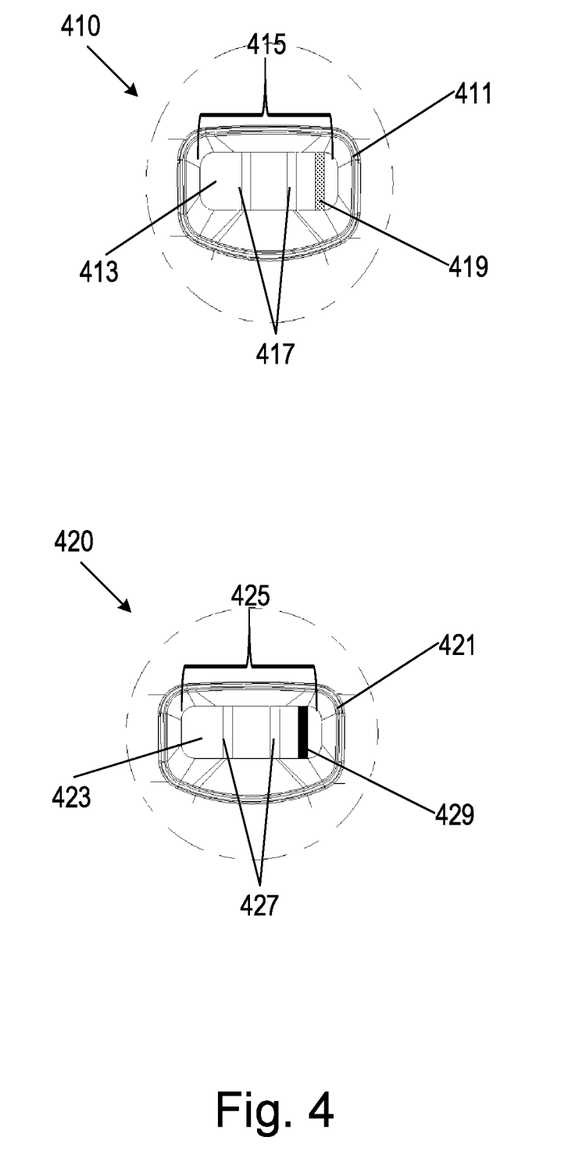
FIG. 4 illustrates a fourth bottom perspective view 410 of a part of a fourth type of test strip adaptor, and a fifth bottom perspective view 420 of a part of a fifth type of test strip adaptor, according to some embodiments of the present disclosure.

In conjunction with FIG. 2, FIG. 4 illustrates a fourth bottom perspective view 410 of 2A of a fourth type of test strip adaptor 220 in FIG. 2 and a fifth bottom perspective view 420 of 2A of a fifth type of test strip adaptor 220 in FIG. 2, according to some embodiments of the present disclosure.

In some embodiments, the fourth type of test strip adaptor defines test strip opening 411 and encloses test strip 413 to determine a fourth biological property. In some embodiments, reaction area 415 of test strip 413 is exposed from test strip opening 411. Reaction area 415 may include reaction bar 417 with a reaction agent sensitive to the fourth biological property. In some embodiments, reaction area 415 further includes first bar 419 with a first color. In conjunction with FIG. 1 and FIG. 2, one or more image of reaction area 415 may be captured by camera 107 through test strip opening 411, top opening 215, and camera hole 213. In some embodiments, the captured image may include an image of reaction bar 417 and an image of first bar 419 with the first color. The captured images may be analyzed to determine the fourth biological property.

In some embodiments, the fifth type of test strip adaptor defines test strip opening 421 and encloses test strip 423 to determine a fifth biological property. In some embodiments, reaction area 425 of test strip 423 is exposed from test strip opening 421. Reaction area 425 may include reaction bar 427 with a reaction agent sensitive to the fifth biological property. In some embodiments, reaction area 425 further includes second bar 429 with a second color. In conjunction with FIG. 1 and FIG. 2, one or more image of reaction area 425 may be captured by camera 107 through test strip opening 421, top opening 215, and camera hole 213. In some embodiments, the captured image may include an image of reaction bar 427 and an image of second bar 429 with the second color. The captured images may be analyzed to determine the fifth biological property.

Figure 5:
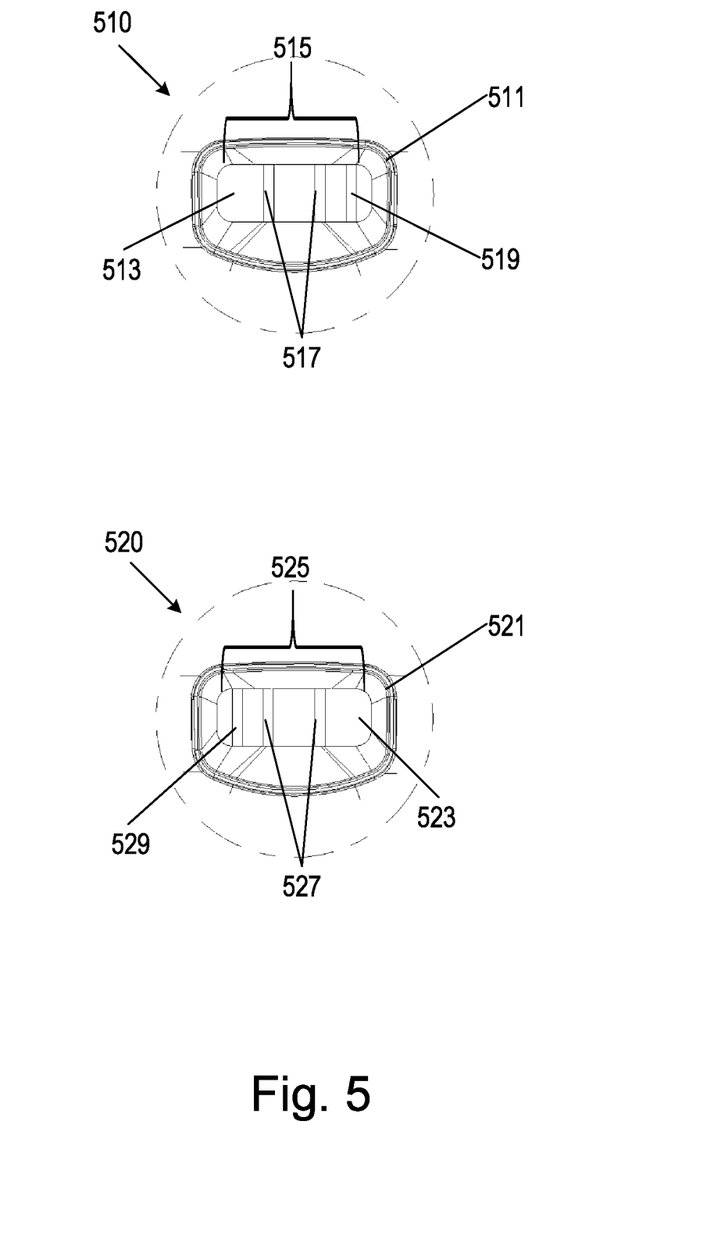
FIG. 5 illustrates a sixth bottom perspective view 510 of a part of a sixth type of test strip adaptor, and a seventh bottom perspective view 520 of a part of a seventh type of test strip adaptor, according to some embodiments of the present disclosure.

In conjunction with FIG. 2, FIG. 5 illustrates a sixth bottom perspective view 510 of 2A of a fourth type of test strip adaptor 220 in FIG. 2 and a seventh bottom perspective view 520 of 2A of a fifth type of test strip adaptor 220 in FIG. 2, according to some embodiments of the present disclosure.

In some embodiments, the sixth type of test strip adaptor defines test strip opening 511 and encloses test strip 513 to determine a sixth biological property. In some embodiments, reaction area 515 of test strip 513 is exposed from test strip opening 511. Reaction area 515 may include reaction bar 517 with a reaction agent sensitive to the sixth biological property. In some embodiments, reaction area 515 further includes first identification mark 519 disposed adjacent to a first side of reaction bar 517. In conjunction with FIG. 1 and FIG. 2, one or more image of reaction area 515 may be captured by camera 107 through test strip opening 511, top opening 215, and camera hole 213. In some embodiments, the captured image may include an image of reaction bar 517 and an image of first identification mark 519. The captured images may be analyzed to determine the sixth biological property.

In some embodiments, the seventh type of test strip adaptor defines test strip opening 521 and encloses test strip 523 to determine a seventh biological property. In some embodiments, reaction area 525 of test strip 523 is exposed from test strip opening 521. Reaction area 525 may include reaction bar 527 with a reaction agent sensitive to the seventh biological property. In some embodiments, reaction area 525 further includes second identification mark 529 disposed adjacent to a second side of reaction bar 527. In conjunction with FIG. 1 and FIG. 2, one or more image of reaction area 525 may be captured by camera 107 through test strip opening 521, top opening 215, and camera hole 213. In some embodiments, the captured image may include an image of reaction bar 527 and an image of second identification mark 529. The captured images may be analyzed to determine the seventh biological property.

Figure 6:
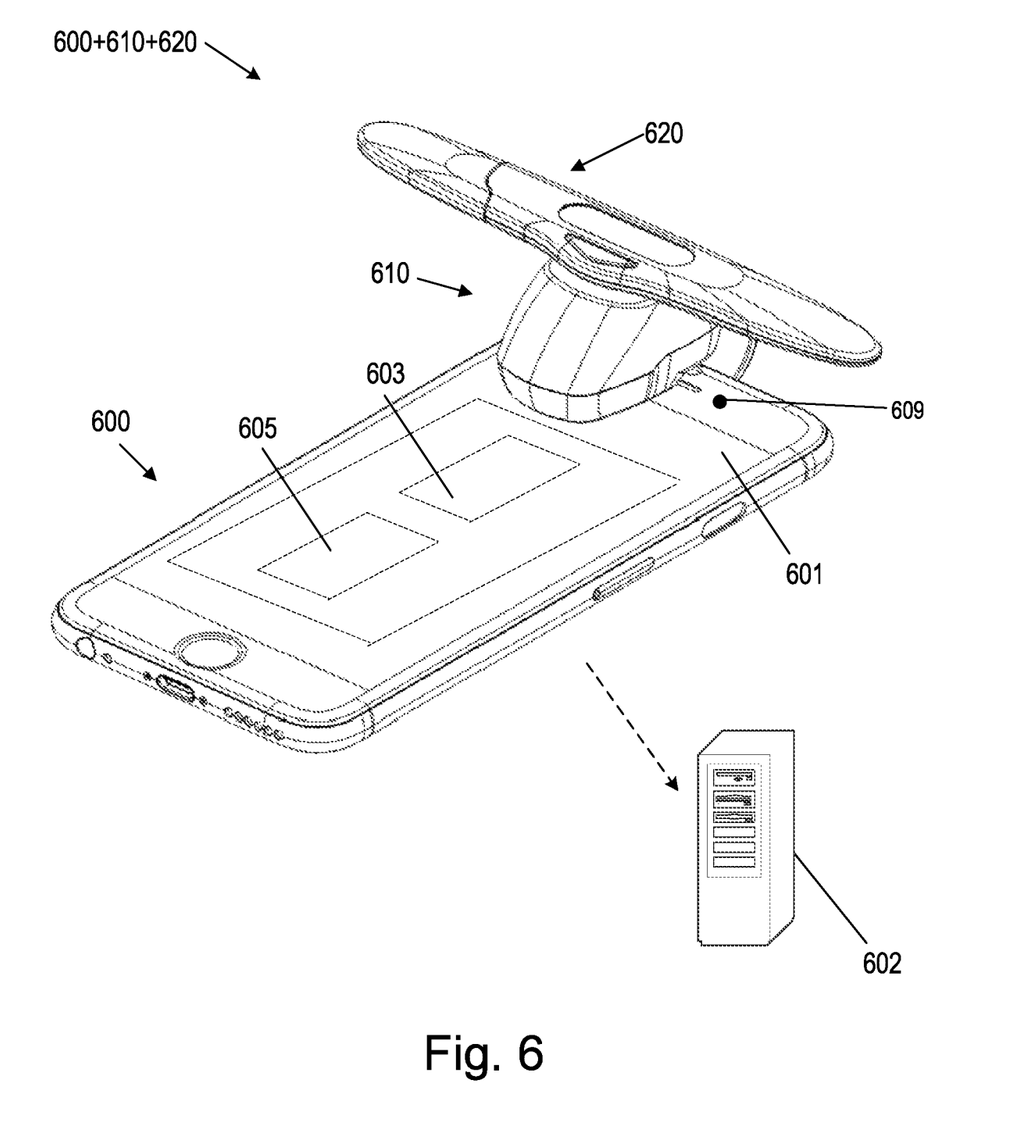
FIG. 6 illustrates a first perspective view of mobile computing device 600, mobile computing device adaptor 610 and test strip adaptor 620, according to some embodiments of the present disclosure.

FIG. 6 illustrates a perspective view of mobile computing device adaptor 610 and test strip adaptor 620 disposed over a camera of mobile computing device 600, according to some embodiments of the present disclosure. In some embodiments, in conjunction with FIG. 1, mobile computing device 600 may be mobile computing device 100. In some embodiments, in conjunction with FIG. 2, mobile computing device adaptor 610 may be mobile computing device adaptor 210, and test strip adaptor 620 may be test strip adaptor 220.

In some embodiments, mobile computing device 600 includes processor 603 and memory 605. In some embodiments, mobile computing device 600 also includes screen 601 and sensor 609 disposed on a same surface of mobile computing device 600. Mobile computing device adaptor 610 is configured to couple to mobile computing device 600 and disposed over the camera of mobile computing device 600 adjacent to sensor 609. Test strip adaptor 620 is configured to couple to mobile computing device adaptor 610.

As set forth above, in conjunction with FIG. 2, light transmitted from screen 601 is configured to travel through mobile computing device adaptor 610 (e.g., through light port 211 and top opening 215) and test strip adaptor 620 (e.g., through test strip opening 223) to a reaction area of a test strip enclosed in test strip adaptor 620. The light transmitted from screen 601 may illuminate the reaction area and the camera of mobile computing device 600 is configured to capture an image of the reaction area through test strip adaptor 620 (e.g., through test strip opening 223) and mobile computing device adaptor 610 (e.g., through top opening 215 and camera hole 213). The captured image may be saved as a file in memory 605. The saved image file may be locally analyzed by processor 603 or remotely analyzed by server 602 to determine a biological property.

Figure 7:
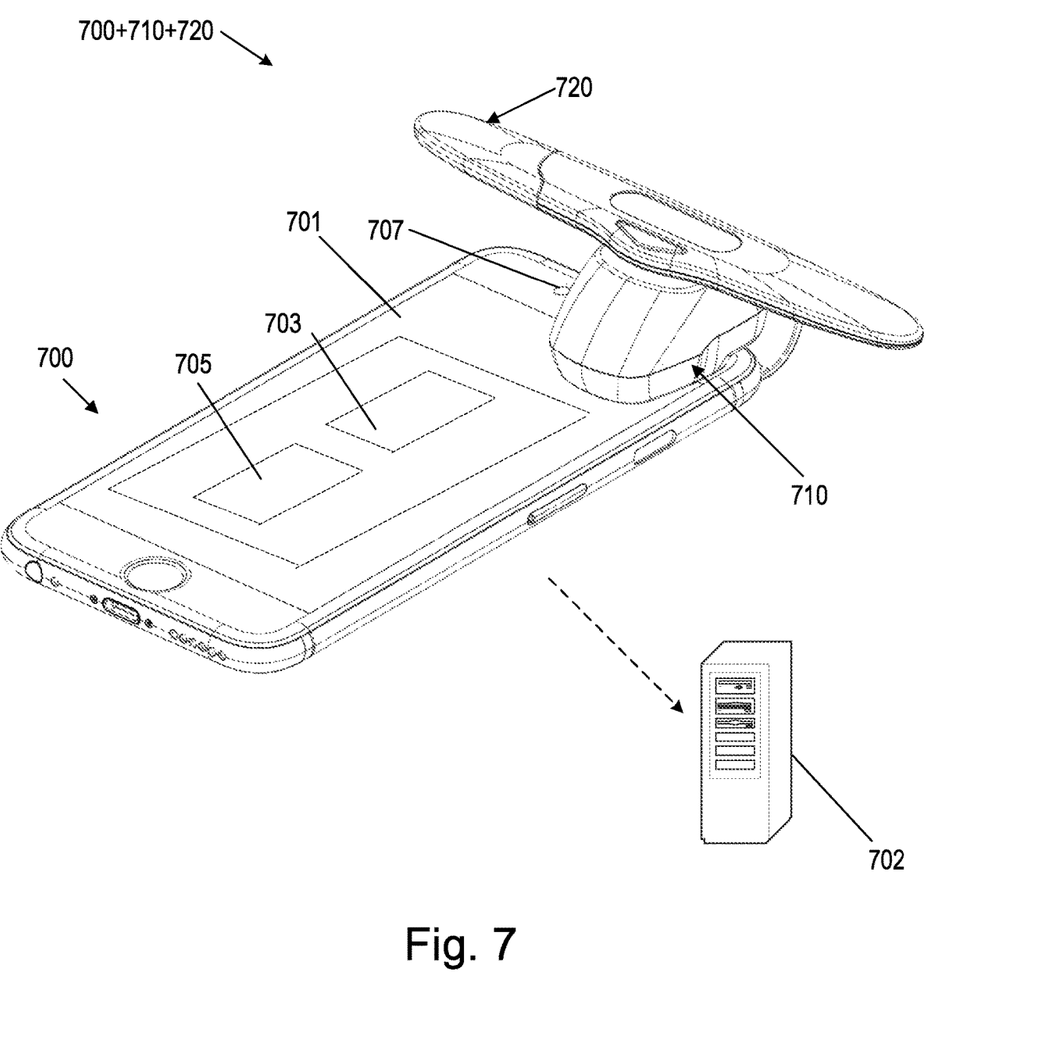
FIG. 7 illustrates a second perspective view of mobile computing device 700, mobile computing device adaptor 710 and test strip adaptor 720, according to some embodiments of the present disclosure.

FIG. 7 illustrates a perspective view of mobile computing device adaptor 710 and test strip adaptor 720 disposed over a sensor, which is not and cannot function as a camera, of mobile computing device 700, according to some embodiments of the present disclosure. In some embodiments, in conjunction with FIG. 1, mobile computing device 700 may be mobile computing device 100. In some embodiments, in conjunction with FIG. 2, mobile computing device adaptor 710 may be mobile computing device adaptor 210, and test strip adaptor 720 may be test strip adaptor 220.

In some embodiments, mobile computing device 700 includes processor 703 and memory 705. In some embodiments, mobile computing device 700 also includes screen 701 and camera 707 disposed on a same surface of mobile computing device 700. Mobile computing device adaptor 710 is configured to couple to mobile computing device 700 and disposed over the sensor of mobile computing device 700 adjacent to camera 707. Test strip adaptor 720 is configured to couple to mobile computing device adaptor 710.

Not like the implementations illustrated in FIG. 6, mobile computing device adaptor 710 and test strip adaptor 720 are disposed at an incorrect position (i.e., over the sensor of mobile computing device 700). Therefore, even though the light transmitted from screen 701 may still illuminate a reaction area of a test strip enclosed in test strip adaptor 720, the image cannot be obtained by camera 707. On the contrary, camera 707 may capture other images irrelevant to determining the biological property. For example, camera 707 may capture the user's image, which causes concerns in privacy rights.

Figure 8:
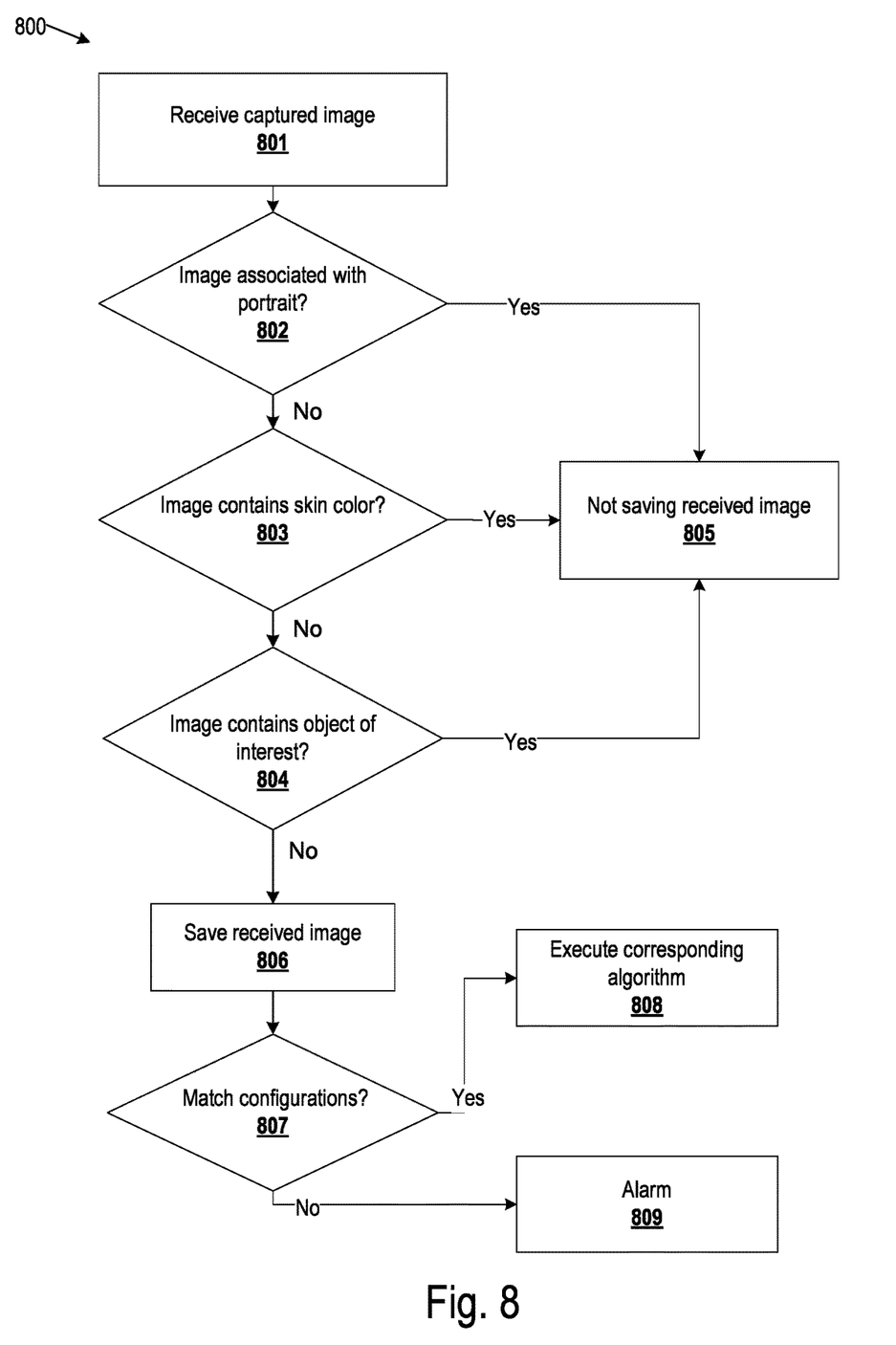
FIG. 8 is a flowchart of method 800 to process an image that may include sensitive information to determine a biological property associated with a test strip adaptor of FIG. 1 to FIG. 7, according to some embodiments of the present disclosure.

FIG. 8 is a flowchart of method 800 to process an image that may include sensitive information to determine a biological property associated with a test strip adaptor, according to some embodiments of the present disclosure. Method 800 may include one or more operations, functions, or actions illustrated by one or more blocks. Method 800 may be performed by a mobile computing device or a server that the mobile computing device communicates with. Although the blocks of method 800 and other methods described herein are illustrated in sequential orders, these blocks may also be performed in parallel, or in a different order than those described herein. Also, the various blocks may be combined into fewer blocks, divided into additional blocks, or eliminated based upon the desired implementation. Method 800 may begin in block 801.

In block 801, in conjunction with FIG. 6, in some embodiments, a first image captured by the camera of mobile computing device 600 may be received by mobile computing device 600 or server 602 from mobile computing device 600. The received first image may be an image of a reaction area of a test strip enclosed in test strip adaptor 620. It should be noted that mobile computing device adaptor 610 is disposed at a position on mobile computing device 600, where mobile computing device adaptor 610 covers the camera (e.g., camera 707) of mobile computer device 600.

The mobile computing device adaptor may be disposed at a different position on the mobile computing device. As an illustrating using FIG. 7, mobile computing device adaptor 710 does not cover camera 707 of mobile computing device 700. A second image captured by camera 707 may be received by mobile computing device 700 or server 702 from mobile computing device 700. Unlike the received first image, the received second image is not an image of the reaction area of the test strip enclosed in test strip adaptor 720, because mobile computing device adaptor 710 does not over camera 707. The received second image may include sensitive information, such as a part of user's face, a part of a mark on user's body (e.g., a tattoo), or an object including user's privacy information (e.g., user's identification card or license plate). Block 801 may be followed by block 802.

In block 802, the received image is analyzed to determine whether the received image is associated with a portrait. In some embodiments, a portrait may refer to an image that includes one or more human facial characteristic points. For example, a portrait may be an image that includes, without limitation, one or more contours of a face, one or more eyes, a nose, etc. One or more facial recognition approaches may be used to analyze the received image and determine whether the received image is associated with a portrait. In response to the received image being determined to be associated with a portrait, block 802 may be followed by block 805.

In block 805, the received image is not to be saved as a file. In some embodiments, a write operation associated with an application program interface (API) will not be executed by mobile computing device 600/700 or server 602/702. Therefore, the received image will neither be written as a file nor read from the file. In addition, this received image will generally be overwritten by a later received image. Accordingly, the received image, if determined to be associated with a portrait, may be discarded.

On the other hand, in response to the received image being determined not to be associated with a portrait, block 802 may be followed by block 803.

In block 803, the received image is analyzed to determine whether the received image contains skin color information. For example, the received image may include a tattoo in whole or in part on skin. A tattoo may reveal personal information of a user but cannot be detected in block 802. Since the tattoo is placed on human skin, detecting the color information of the skin on which the tattoo is placed from the received image helps to earmark such an image as containing personal information. One or more image color histogram approaches may be used to determine whether the received image contains skin color information. In some embodiments, the received image may be converted to a first color histogram in a color space. The first color histogram may be compared to a set of prestored color histograms corresponding to one or more common human skin colors. In response to a difference between the first color histogram and the set of the prestored color histograms being smaller than a threshold, the received image is determined to contain skin color information. In response to the received image being determined to contain skin color information, block 803 may be followed by block 805. Accordingly, the received image including skin color information may be discarded.

In response to the received image is determined not to contain skin color information, block 803 may be followed by block 804.

In block 804, the received image is analyzed to determine whether the received image contains an object of interest. Some examples of the object may include personal information of a user, such as an identification card or a license plate of the user. One or more image recognition approaches may be used to analyze the received image and determine whether the received image contains the object of interest. In response to the received image is determined to contain the object of interest, block 804 may be followed by block 805. Accordingly, the received image including the object of interest may be discarded.

In response to the received image being determined not to contain the object of interest, block 804 may be followed by block 806.

In block 806, the received image is saved as a file. In some embodiments, a write operation associated with an application program interface (API) is executed by mobile computing device 600/700 or server 602/702 to write the received image as a file. After the received image is written as a file, it can be retrievable from the file also.

In some embodiments, an Android device includes two file storage areas: the internal storage and the external storage. A file saved in the internal storage is accessible by only a specific application associated with the file. In response to the application is uninstalled, the system removes this file from the internal storage. A file saved in the external storage may be read outside the user's control. In some embodiments, the received image is written as a file and saved in the internal storage by default. To save the written file in the internal storage, several functions may be called. Some example functions may include, but not limited to, getFilesDir( ) which returns a file representing an internal directory for the application, getCacheDir( ) which returns a file representing an internal directory for the application's temporary cache files, File( ) which creates a new file in a directory, and openFileOutput( ) which writes to a file in an internal directory.

In some embodiments, a user may save the received image by creating a file in an internal storage of an iOS device for the received image. Any created file often inherits the permissions associated with the current user and process. There are two parts to creating a file: creating a record for the file in the file system of the iOS device and filling the file with content. In the iOS, some routines may be used to create files. Example routines may include, but not limited to, createFileAtPath:contents:attributes:, writeToURL: atomically:, writeToURL:atomically:, writeToURL:atomically:encoding:error:, and writeToURL:atomically:.

In some embodiments, in a Microsoft Window device, CreateFile function may be called to create a new file or open an existing file in a storage (e.g., a hard disk) of the device. The operating system may assign a unique identifier, handle, to each file that is opened or created using CreateFile. An application can use this handle with functions that read from, write to, and describe the file. Block 806 may be followed by block 807.

Referring back to the received first image being an image of a reaction area of a test strip enclosed in test strip adaptor 620, the processing of the received first image may bypass blocks 802, 803, and 804 and proceed to block 806 so that the received first image is saved as a file.

Referring back to the received second image including sensitive information, the received second image may end up at block 805 so that the received second image is not saved as a file and will be overwritten by another received image shortly.

In block 807, in conjunction with FIG. 3, FIG. 4, and FIG. 5, the received image may be an image of reaction area 315, 325, 335, 415, 425, 515, or 525 of test strip 313, 323, 333, 413, 423, 513, or 523, respectively. In some embodiments, each of test strips 313, 323, 333, 413, 423, 513, and 523 is configured to detect a unique biological property. As set forth above, any of reaction area 315, 325, 335, 415, 425, 515, and 525 includes corresponding characteristic configuration (e.g., protrusion 329/339, first colored bar 419, second colored bar 429, identification mark 519/529). The characteristic configurations may be prestored in mobile computing device 600/700 or server 602/702. In some embodiments, mobile computing device 600/700 or server 602/702 is configured to compare the received image against the prestored configurations and determine whether the received image matches the prestored configurations. In response to the received image being determined to match the prestored configurations, block 807 may be followed by block 808. Alternatively, in response to the received image being determined not to match the prestored configurations, block 807 may be followed by block 809.

In block 808, mobile computing device 600/700 or server 602/702 is configured to execute a prestored algorithm. As an illustration, suppose the received image includes an image of protrusion 329. Mobile computing device 600/700 or server 602/702 is configured to execute a prestored algorithm associated with a particular biological property that test strip 323 is configured to determine (e.g., the second biological property set forth above). Based on the prestored algorithm and the received image, mobile computing device 600/700 or server 602/702 may determine the second biological property.

In block 809, mobile computing device 600/700 or server 602/702 is configured to generate an alarm signal. For example, the user may erroneously use a test strip adaptor enclosing an incorrect test strip. Therefore, mobile computing device 600/700 or server 602/702 is configured to generate an alarm signal for the user and not to determine the biological property.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method to process an image to determine a biological property associated with a test strip in a test strip adaptor, the method comprising:
   receiving the image captured by a mobile computing device;
   determining whether the image includes sensitive information;
   in response to determining that the image includes sensitive information,
      overwriting the image with a later received image before the image can be saved as a file; and
   in response to determining that the image does not include sensitive information,
      identifying a characteristic configuration associated with the test strip, and
      determining the biological property based on the image and the characteristic configuration.

2. The method of claim 1, wherein determining the image that includes sensitive information further includes: determining whether the image is associated with a portrait.

3. The method of claim 1, wherein determining the image that includes sensitive information further includes: determining whether the image includes a color associated with a skin color of a human.

4. The method of claim 1, wherein determining the image that includes sensitive information further includes: determining whether the image includes an object of interest.

5. The method of claim 1, the method further comprises:
   prior to determining the image that does not include sensitive information:
   illuminating the test strip with a light transmitted from the screen of the mobile computing device; and capturing the image by a camera of the mobile computing device.

6. The method of claim 1, the method further comprises:
   prior to determining that the image includes sensitive information, capturing the image by a camera of the mobile computing device, wherein a mobile computing device adaptor, coupled to the test strip adaptor, is placed on the mobile computing device but without completely covering the camera of the mobile computing device.

7. The method of claim 1, in response to determining that the image does not include sensitive information, the method further includes executing a write operation associated with an application program interface (API) on the image.

8. The method of claim 1, wherein the identifying the characteristic configuration of the test strip further includes determining whether the characteristic configuration matches a prestored characteristic configuration.

9. The method of claim 8, in response to the characteristic configuration determined to match the prestored characteristic configuration, the method further includes executing an algorithm specifically corresponding to the biological property.

10. The method of claim 8, in response to the characteristic configuration determined not to match the prestored characteristic configuration, the method further includes generating an alarm signal to prevent from determining the biological property.

11. The method of claim 1, wherein the characteristic configuration is a protrusion of the test strip adaptor.

12. The method of claim 1, wherein the characteristic configuration is a mark on the test strip.

13. A non-transitory computer-readable storage medium that includes a set of instructions which, in response to execution by a processor of a computer system, cause the processor to implement a method to process an image to determine a biological property associated with a test strip in a test strip adaptor, wherein the method comprises:
receiving the image captured by a mobile computing device;
determining whether the image includes sensitive information;
in response to determining that the image includes sensitive information,
overwriting the image with a later received image before the image can be saved as a file; and
in response to determining that the image does not include sensitive information,
identifying a characteristic configuration associated with the test strip, and
determining the biological property based on the image and the characteristic configuration.

14. The non-transitory computer-readable storage medium of claim 13, wherein determining the image that includes sensitive information further includes determining whether the image is associated with a portrait, whether the image includes a color associated with a skin color of human, or whether the image includes an object of interest.

15. The non-transitory computer-readable storage medium of claim 13, wherein the method further comprises:
prior to determining that the image does not include sensitive information:
illuminating the test strip with a light transmitted from the screen of the mobile computing device; and capturing the image by a camera of the mobile computing device; or
prior to determining that the image includes sensitive information:
capturing the image by a camera of the mobile computing device, wherein a mobile computing device adaptor, coupled to the test strip adaptor, is placed on the mobile computing device but without completely covering the camera of the mobile computing device.

16. The non-transitory computer-readable storage medium of claim 13, in response to determining that the image does not include sensitive information, the method further includes executing a write operation associated with an application program interface (API) on the image.

17. A computer system configured to process an image to determine a biological property associated with a test strip in a test strip adaptor, wherein the computer system comprises:
a processor; and
a non-transitory computer-readable medium having stored thereon instructions that, in response to execution by the processor, cause the processor to:
receive the image captured by a mobile computing device;
determine whether the image includes sensitive information;
in response to determining that the image includes sensitive information,
overwrite the image with a later received image before the image can be saved as a file; and
in response to determining that the image does not include sensitive information,
identify a characteristic configuration associated with the test strip, and
determine the biological property based on the image and the characteristic configuration.

18. The computer system of claim 17, wherein the non-transitory computer-readable medium having stored thereon additional instructions that, when executed by the processor, cause the processor to determine whether the image is associated with a portrait, whether the image includes a color associated with a skin color of human, or whether the image includes an object of interest.

19. The computer system of claim 17, wherein the computer system is the mobile computing device or a remote server.

20. The computer system of claim 17, wherein the non-transitory computer-readable medium having stored thereon additional instructions that, when executed by the processor, cause the processor to, in response to determining that the image does not include sensitive information, execute a write operation associated with an application program interface (API) on the image.

* * * * *